United States Patent [19]

Wang

[11] Patent Number: 5,558,875
[45] Date of Patent: Sep. 24, 1996

[54] METHOD OF PREPARING COLLAGENOUS TISSUE

[76] Inventor: Su Wang, 858 59 St., Brooklyn, N.Y. 11220

[21] Appl. No.: 254,685

[22] Filed: Jun. 6, 1994

[51] Int. Cl.[6] .............................. A61F 13/00; A61F 2/00; A61K 35/34; A61K 38/17

[52] U.S. Cl. ..................... 424/422; 424/423; 424/548; 424/549; 424/569; 424/572; 424/583; 530/356; 514/21; 623/901

[58] Field of Search .................................. 424/422, 423, 424/572, 569, 548, 549, 583; 435/240.2; 530/356; 623/1, 11, 901, 2; 514/21

[56] References Cited

U.S. PATENT DOCUMENTS

| | | | |
|---|---|---|---|
| 3,927,422 | 12/1975 | Sawyer | 3/1 |
| 4,082,507 | 4/1978 | Sawyer | 8/94.11 |
| 4,319,363 | 3/1982 | Ketharanathan | 3/1.4 |
| 4,597,762 | 7/1986 | Walter et al. | 623/1 |
| 4,670,286 | 6/1987 | Nyilas et al. | 427/2 |
| 4,687,482 | 8/1987 | Hanson | 623/1 |
| 4,776,853 | 10/1988 | Klement et al. | 8/94.11 |
| 4,778,467 | 10/1988 | Stensaas et al. | 623/12 |
| 4,789,663 | 12/1988 | Wallace et al. | 514/21 |
| 4,814,120 | 3/1989 | Huc et al. | 264/28 |
| 4,902,289 | 2/1990 | Yannas | 623/1 |
| 4,970,298 | 11/1990 | Silver et al. | 530/356 |
| 4,975,526 | 12/1990 | Kuberasampath et al. | 530/350 |
| 4,990,131 | 2/1991 | Dardik et al. | 600/36 |
| 5,019,393 | 5/1991 | Ito et al. | 424/423 |
| 5,131,907 | 7/1992 | Williams et al. | 600/36 |
| 5,166,187 | 11/1992 | Collombel et al. | 514/21 |
| 5,171,273 | 12/1992 | Silver et al. | 623/13 |
| 5,171,574 | 12/1992 | Kuberasampath et al. | 424/423 |
| 5,207,710 | 5/1993 | Chu et al. | 623/16 |
| 5,215,541 | 6/1993 | Nashef et al. | 8/94.11 |
| 5,447,536 | 9/1995 | Giradot et al. | 8/94.11 |
| 5,480,427 | 1/1996 | Kelman et al. | 623/6 |

OTHER PUBLICATIONS

Walter, M. et al., "Annales de Chirurgis, Chirurgie thoracique et cardio-vasculaire," vol. 48(9), pp. 870–875. French original and English translation 1994.

Hosokawa, R., "Kyushu Shika-shi," vol. 43(6), pp. 914–927. Japanese original and English translation 1989.

Van Gulik, T. M. et al., "The Netherlands Journal of Surgery," vol. 39(3), pp. 90–94 1987.

Wasserman, A. J. et al., "Scanning Microscopy," vol. 3(4), pp. 1183–1200 1989.

Charpentier, A. et al., "Comptes Rendus," vol. 272(1, Series D), pp. 178–179. French original and English translation Jan. 1971.

*Primary Examiner*—Chhaya D. Sayala
*Assistant Examiner*—Kristin K. Larson

[57] ABSTRACT

A process of preparation of a collagenous prosthesis for removing cell membrane proteins from a biological collagenous tissue and preserving elasticity of the collagenous prosthesis comprises the following steps: (a) soaking the tissue in an organic detergent for a sufficient time to disrupt the cell membrane and to solubilize the cellular membrane proteins of the collagenous tissue; (b) extracting and removing the cellular membrane proteins from the collagenous tissue by mechanical washing to obtain the collagenous prosthesis; (c) preserving the collagenous prosthesis in alcohol.

7 Claims, No Drawings

METHOD OF PREPARING COLLAGENOUS TISSUE

BACKGROUND

1. Field of the Invention

This invention relates to the preparation of collagenous tissue. In particular, it relates to prostheses made from collagenous tissue.

2. Description of the Prior Art

Despite significant advances in surgery and medicine, there is still no satisfactory prosthesis available for small arterial replacements (less than 3 mm in diameter). The requirements for an ideal prosthetic material are: 1) biocompatible or non-antigenic; 2) mechanical compatibility or matched elasticity; 3) stability under continuous stress; 4) resistant to thrombosis formation; 5) ease and low cost in fabrication; and 6) ease of sterilization. Unfortunately, there has been no existing man-made prosthesis that meets all these criteria, especially for small-diameter arterial prosthesis such as a graft for coronary artery bypass.

Collagen, the major protein forming the blood vessel and skin of all living organisms, is an ideal material for blood vessel prosthesis with no antigenicity and good elasticity. However, all the previous studies and patents in making collagen prostheses for blood vessel replacements failed to reach a acceptable patency rate (>90%) due to high incidence of thrombosis formation, especially in small-diameter blood vessel. Some examples of the prior art in making collagen prosthesis are set forth in the patents briefly described below.

The U.S. Pat. No. 4,082,507 to Sawyer describes a method to chemically modify collagen surfaces to negative charges and then subsequent tanning with glutaraldehyde. He suggests that negative charged blood flow surface may prevent thrombosis formation. The patency of the negatively charged collagen prostheses is 75% within 10 months (Sawyer P N: Patency of Small-Diameter Negatively Charged Glutaraldehyde-Tanned Grafts, in Sawyer P N (eds):MODERN VASCULAR GRAFTS. New York, McGraw-Hill Book Company, 1987, p 163–180).

The U.S. Pat. No. 4,319,363 to Ketharanathan describes a method to obtain a type I collagen prosthesis. After being subjected to glutaraldehyde tanning, all the prostheses are thrombosed when their diameters are less than 4 mm.

The U.S. Pat. No. 4,597,762 to Walter describes a process and an apparatus to obtain a type I collagen prosthesis with a patency rate of 14% within 4 weeks.

The U.S. Pat. No. 4,776,853 to Klement et al disclosed a process comprised of extracting of a tissue by a series of detergent and enzymatic treatments and storage of the tissue in physiologic buffered solutions.

The U.S. Pat. Nos. 4,787,900 and 4,902,289 to Yannas describe a method for forming a multilayer blood vessel prosthesis with biodegradable material and collagen.

The U.S. Pat. No 4,814,120 to Huc et al introduces a process to prepare collagen gel and subsequently drying the gel to form a collagen tube.

The U.S. Pat. No. 4,990,131 to Dardik et al describes a method of tanning umbilical cord vessels with glutaraldehyde under cyclic pressure so that tanning agent can pass through the media wall.

None of the above patents have fulfilled the requirements for an ideal small-diameter blood vessel prosthesis and achieved an adequate patency rate in small arterial transplantation (less than 3 mm in diameter). The possibilities for their failures to obtain satisfactory patency in small-diameter vascular replacement could be due to following reasons: 1) type I collagen, a thrombogenic protein, was used for the blood flow surface; 2) glutaraldehyde tanning of the blood vessel resulted in decreased vascular elasticity and compliance; 3) enzyme-digesting caused denaturation of elastin and collagen structures; and 4) endothelial and smooth muscle cells acting as antigens were not completely removed from the blood vessel and cause tissue rejection.

The advantages of the present invention include that: 1) high patency rate obtained in an arterial prosthesis with 1.2 mm in diameter, 2) simplicity for fabrication and sterilization; 3) preservation of tissue elasticity and compliance therefore suitable for small-diameter blood vessel implants; and 4) decreased antigenicity with extensive washing that may minimize aneurysm formation and calcification. The procedure can be carried out at room temperature without requirement of accurate pH or other buffers. Sterilization of the graft is achieved by detergent washing and alcohol preservation without requirement of other antibiotic treatments and crosslinking agents.

Use of organic surfactants to treat a heart valvular tissue has been described by several prior patents in an attempt to reduce tissue calcification. The following patents disclosed various techniques to treat tissue with surfactants in combination with glutaraldehyde fixation.

The U.S. Pat. No. 4,323,358 to Lentz and Pollock discloses treatment of glutaraldehyde-fixed tissue with a water-soluble salt of sulfated aliphatic alcohol to reduce tissue calcification.

The U.S. Pat. No. 4,553,974 to Dewanjee discloses a process for the treatment of collagenous tissue with surfactants prior to fixation for a period of 2 to 6 hours in order to promote the growth of endothelial cells.

The U.S. Pat. No. 5,215,541 to Nashef et al discloses treatment of a glutaraldehyde-fixed tissue with a variety of anionic and nonionic surfactants to reduce calcification in a heart valve.

Although calcification was reduced in the procedure described by the prior art disclosures using a subcutaneous model with implantation of a valvular tissue under rat skin, the implanted valve was not under a physiological pressure and had no contact with blood flow. Calcification still occurred as the valves were implanted in the aortic position during long-term implantation (Thubrikar M J, Nolan S P, Deck J D, et al: Intrinsic Calcification of T6-processed and Control Porcine and Bovine Bioprostheses in Calves. Trans Am Soc Artif Intern Organs 1983;24:245–249). Furthermore, none of the aforesaid prior art disclosures recognized the importance of the tissue antigens at cell membrane surface that cause rejection and consequent degeneration of the implanted tissue. All of the above prior art disclosures have used glutaraldehyde to fix the tissue before or after the treatment of surfactants. The disadvantages of glutaraldehyde fixation include: 1) antigenic cell proteins cannot be removed from the tissue after fixation process and 2) there is a decrease in tissue elasticity by fixation that promotes thrombosis and prevents angiogenesis of the tissue. In addition, the duration of surfactant treatment in the above prior art disclosures was usually less than 2 days without any mechanical and alcohol washing.

In the present invention, the biological collagenous tissue is processed by extensive detergent soaking and washing to remove the cellular elements, mainly lipid membrane proteins, and to maintain the mechanical property of the tissue such as compliance, defined as a percentage increase in blood vessel diameter followed by an elevation of the intraluminal pressure, of a blood vessel. The processed tissue is suitable not only for small-diameter blood vessel implants, but also for other tissue implants including heart valve, venous valve, skin and cornea.

OBJECTIVES OF THE INVENTION

Therefore it is the objective of the present invention to prepare a biological collagenous tissue by removal of the cellular membrane proteins from the tissue therefore to reduce antigenicity and rejection after implantation.

It is another object of the present invention to provide good elasticity of the collagenous tissue by preserving in a 70% alcohol solution rather than use of glutaraldehyde fixation.

It also is an object of the present invention to provide an inexpensive collagen prosthesis from human or animal origin prepared by extracting the cellular membrane proteins with detergents assisted with mechanical washing.

It is an additional object of the present invention to prevent thrombosis formation by matching the compliance of processed artery to the compliance of recipient artery by combining detergent washing with alcohol preservation.

SUMMARY OF THE INVENTION

The present invention provides a preparation process for making collagenous tissue comprising the following consecutive steps:

(1) soaking the tissue in an organic detergent, such as sodium dodecyl sulfate (SDS), to solubilize the cell membrane proteins in the collagenous tissue;

(2) washing and removing the cellular membrane proteins from the tissue by mechanical shaking and stirring;

(3) preserving the tissue in alcohol such as ethyl alcohol;

(4) matching the mechanical properties of the processed prosthetic tissue with those of the recipient tissue before implantation.

DETAILED DESCRIPTION

The process for the preparation of the collagen prostheses according with the invention comprises essentially four steps which will now be described in detail:

Step 1. Disruption of cell membrane in collagenous tissue:

The tissues, such as blood vessel, skin, heart valve, venous valve, and cornea, are removed from either a human or animal and are soaked in an organic detergent. The detergents within the scope of the present invention include ionic detergents, such as sodium dodecyl sulfate (SDS) with 4 to 20 carbon atoms and sodium deoxycholate; or nonionic detergents, such as TRITON X-100 (trademark) and octyl-glucoside. The detergents are amphipathic molecules and possess both hydrophobic (lipid-loving) and hydrophilic (water-loving) regions. These detergents can disrupt cell membrane by intercalating phospholipid bilayers and solubilizing membrane lipids and proteins of the tissue. The cell membrane proteins are antigens and therefore can induce tissue rejection after implantation between different individuals or species. The pretreatment of tissue with the detergents not only dissolves the cell antigenic proteins, but also sterilizes the collagenous tissue by destroying bacteria and viruses. The detergents solubilize the cell membrane proteins by forming mixed micelles of detergent, phospholipid, and integral membrane proteins.

In accordance with the present invention, the tissue is treated with a detergent at a temperature range from 4° C. to 37° C. Room temperature is preferable. The duration of tissue soaking in a detergent varies from 2 to 20 days depending on the size and thickness of the tissue, preferably for around 7 days.

The effective amount of the detergent used for soaking the tissue depends on the total weight of the treated tissue, preferably in a range of 1% to 10% of the total tissue weight.
Step 2. Removal of soluble proteins from the tissue:

After extensive soaking of the tissue in a detergent, mechanical washing is required to remove the soluble protein micelles from the tissue. The washing procedure consists of mechanical shaking for 4 to 10 hours using a mechanical shaker and subsequent stirring for another 4 to 10 hours using a magnetic stirrer. All the washing procedures are carried out at room temperature. The solution for the tissue washing is the stone solution used for the soaking process of step (1). If a tubular tissue such as a blood vessel is used as a prosthesis, the effectiveness of the washing procedure is further enhanced by a pulsatile pressure in the lumen of the tissue which opens up the porous vascular tissue and allows detergents to pass through the tissue and remove the soluble detergent-bound membrane proteins from the blood vessel. A roller pump can provide such intraluminal pulsatile pressure in a range from 0 to 100 mmHg inside the blood vessel. The process of detergent washing with the pulsatile pressure in the blood vessel is continued for about 4 hours prior to mechanical shaking and stirring.

In accordance with the present invention, it is preferable to rinse the tissue with distilled water for 1 to 4 hours after each mechanical washing with the detergent. The mechanical washing procedure is repeated for 2 to 6 times depending on the tissue size, preferably for three times.
Step 3. Washing and preservation with alcohol:

A further washing is achieved with an alcohol solution, preferably ethyl alcohol with a concentration range from 40% to 85%. The detergent-washed tissue is soaked and stirred in an alcohol solution starting with a low concentration, preferably a 40% alcohol solution for 4 to 10 hours. The final mechanical washing, is achieved by 70% alcohol solution for about 4 to 10 hours. The tissue after the final alcohol washing is preserved in 70% alcohol until needed for implantation. The tissue is stored in a temperature range from −192° C. to 22° C. depending on the duration of the storage. The lower temperature is used for longer storage.
Step 4. Mechanical testing before implantation.

After the collagenous tissue is washed with detergent and 70% ethyl alcohol, the mechanical properties of the tissue will be analyzed. If it is a blood vessel, compliance of the extracted blood vessel will be measured and defined as percentage diameter change in a given pressure increment. The compliance of the prosthesis is one of the important determinants for the patency rate of a small-diameter blood vessel. Therefore, the compliance value of the processed artery is required to be estimated and to match closely to the compliance of a recipient artery. In according to this invention, the difference in compliance should not exceed more than 30% between the detergent-washed collagen prosthesis and the recipient artery, preferably less than 10% of the difference in compliance, or in a range of 90% to 110% matching in compliance between donor prostheses and recipient arteries.

The effectiveness of the present invention using a combination of detergent and alcohol treatments in a microvascular tissue was determined by a following animal study.

Sprague-Dawley rats with an average weight of 450 grams were used as recipients. Guinea pig carotid arteries (1.2 mm in diameter) were used as donor arterial xenografts (different species) and transplanted into the carotid position of the recipient Sprague-Dawley rats. The rat carotid artery is an elastic and compliant blood vessel which has similar mechanical properties to the coronary artery. The microsurgery was performed to insert the guinea pig arteries into the rat carotid arteries under a microscope with a 14x magnification. As shown in Table 1, the donor guinea pig arterial xenografts were divided into three groups according to various treatments: group 1= the donor arteries were preserved only in 70% ethyl alcohol without SDS detergent washing; group 2= the donor arteries were soaked and washed with SDS detergent for 7 days and first preserved in 70% ethyl alcohol and then treated with 2% glutaraldehyde solution for 10 minutes before implantation; and group 3= the donor arteries were soaked and washed with SDS detergent for 7 days and preserved in 70% ethyl alcohol without glutaraldehyde fixation. The donor arterial xenografts were interposed in an end-to-end fashion into the recipient rat carotid arteries. The patency rate was evaluated by direct inspection. The compliance is defined as a percentage change in diameter after a pressure rise of 100 mmHg. The compliance values of the guinea pig donor carotid arteries treated with three different methods were compared with the compliance of the rat recipient carotid artery. The value for the compliance match was calculated by dividing the donor arterial compliance by the recipient arterial compliance.

The results in Table 1 indicate that a high patency rate can be obtained by a combination of SDS detergent washing and alcohol preservation which maintains the compliance of the processed blood vessel and may have a potential application in the development of a compliant small-diameter prosthesis for coronary arterial bypass (<3 mm in diameter). The results showed that alcohol alone could lower the tissue compliance when the cellular elements of the tissue were not removed by SDS detergent-washing method (group 1), The combination of SDS detergent and alcohol treatments (group 3) provided the highest compliance value, the closest match of compliance between the collagen prostheses and recipient arteries, and therefore exhibited the highest patency rate than the alcohol preservation only (group 1) and glutaraldehyde fixation (group 2). All the arterial xenografts crosslinked with glutaraldehyde were thrombosed because of the diminished compliance.

TABLE 1

| Groups: | 1) No SDS wash + alcohol No GA | 2) SDS wash + alcohol + GA | 3) SDS wash + alcohol No GA |
|---|---|---|---|
| # of patent grafts/ Total implanted xenografts | 2/6 | 0/6 | 6/6 |
| Compliance of donor guinea pig arteries (% change/100 mmHg) | 12 ± 6 | 7 ± 3 | 31 ± 10 |
| % Compliance match between donor and recipient arteries | 43% | 25% | 110% |
| Patency rates | 33% | 0% | 100% |

*Compliance is expressed as % of diameter changes per 100 mmHg increase in intraluminal pressure.
*Patency rate is expressed as the number of patent xenograft prostheses vs. the total number of implanted prostheses.
*GA = Glutaraldehyde

What I claim is:

1. A process of preparing collagenous prosthesis having elasticity from a biological collagenous tissue consisting of the following steps in order:

(a) soaking the tissue in an organic detergent for a sufficient time to disrupt cell membranes and to solubilize cellular membrane proteins of the collagenous tissue;

(b) washing the tissue with the organic detergent to remove the solubilized cellular membrane proteins;

(c) rinsing the tissue with distilled water to obtain the collagenous prosthesis having elasticity;

(d) storing the prosthesis in alcohol as a means to preserve the elasticity.

2. The process according to claim 1, wherein said organic detergent is an amphipathic molecule having both hydrophobic and hydrophilic regions which bind to lipids and proteins.

3. The process according to claim 1, wherein said tissue of step (a) is soaked in the detergent for 2 to 20 days to disrupt the cell membranes.

4. The process according to claim 1 wherein said tissue is selected from the group consisting of blood vessels, venous valves, heart valves, skin, tendon, bone, pericardium, cornea, and umbilical cord.

5. The process according to claim 4, wherein said blood vessel has a diameter less than 3 mm.

6. The process according to claim 1, wherein said washing of step (b) is mechanical shaking and stirring of the tissue and applying pulsatile pressure to the collagenous tissue.

7. The process according to claim 1, wherein said-organic detergent of step (a) is sodium dodecyl sulfate.

* * * * *